US011147570B2

(12) United States Patent
Mikus et al.

(10) Patent No.: US 11,147,570 B2
(45) Date of Patent: Oct. 19, 2021

(54) METHOD FOR REDUCING BIOFILM FORMATION

(71) Applicant: MISONIX, INCORPORATED, Farmingdale, NY (US)

(72) Inventors: Paul Mikus, Coto de Caza, CA (US); Scott Isola, Deer Park, NY (US); Dan Voic, Cedar Grove, NJ (US); Scott Ludecker, Mount Sinai, NY (US); Alexander Darian, Brightwaters, NY (US)

(73) Assignee: MISONIX, INCORPORATED, Farmingdale, NY (US)

( * ) Notice: Subject to any disclaimer, the term of this patent is extended or adjusted under 35 U.S.C. 154(b) by 314 days.

(21) Appl. No.: 16/269,229

(22) Filed: Feb. 6, 2019

(65) Prior Publication Data

US 2019/0167285 A1    Jun. 6, 2019

Related U.S. Application Data

(62) Division of application No. 14/933,784, filed on Nov. 5, 2015, now Pat. No. 10,299,809.

(60) Provisional application No. 62/078,709, filed on Nov. 12, 2014.

(51) Int. Cl.
    *A61B 17/22*    (2006.01)
    *A61M 1/00*    (2006.01)

(52) U.S. Cl.
    CPC .. *A61B 17/22004* (2013.01); *A61B 2217/005* (2013.01); *A61M 1/85* (2021.05); *A61M 2205/058* (2013.01)

(58) Field of Classification Search
    CPC .... A61B 17/22004; A61B 2017/00761; A61B 2017/320072; A61B 2017/320084; A61B 2217/005; A61M 1/0084; A61M 2205/058
    See application file for complete search history.

(56) References Cited

U.S. PATENT DOCUMENTS

| 5,139,504 A * | 8/1992 | Zelman ............... A61F 9/00736 606/107 |
| 2008/0249553 A1 * | 10/2008 | Gruber ............. A61B 17/32002 606/171 |
| 2011/0196403 A1 * | 8/2011 | Robertson ...... A61B 17/320068 606/169 |
| 2013/0046316 A1 * | 2/2013 | Sullivan ............. A61B 10/0275 606/115 |
| 2013/0165821 A1 | 6/2013 | Freedman et al. |

* cited by examiner

*Primary Examiner* — Kai H Weng
(74) *Attorney, Agent, or Firm* — R. Neil Sudol; Henry D. Coleman

(57) ABSTRACT

A two phase method for reducing the formation of biofilm includes an evacuation of ambient air from a region about the surgical or treatment site, to extract airborne or aerosolized bacteria ejected from the site by the treatment. The extracted bacteria are prevented from settling back onto the cleansed tissue surface, thus at least reducing colonial bacteriological growth and concomitantly exuded biofilm material. A second phase involves the attachment of one or more ultrasonic transducers to the patient over or near a surgical treatment site after the surgery is terminated. Each applied ultrasonic transducer is used to vibrate the patient's tissues at the treatment site to disrupt biofilm formation.

5 Claims, 2 Drawing Sheets

METHOD FOR REDUCING BIOFILM FORMATION

This application is a division of application Ser. No. 14/933,784 filed Nov. 5, 2015, now U.S. Pat. No. 10,299,809. This application also claims the benefit of U.S. Provisional Patent Application No. 62/078,709 filed Nov. 12, 2014.

BACKGROUND OF THE INVENTION

This invention relates to apparatus and method for reducing the formation of biofilm on a wound site particularly a wound site that has been debrided to remove necrotic tissue.

Chronic wound infection represents a significant healthcare problem worldwide. Often the end objective of wound healing is the objective for new therapeutic options. Yet chronic wounds compromise a number of different and complex conditions that each interferes with the healing process. For example, a chronic wound can comprise necrotic tissue in need of debridement, bacterial infection in need of antimicrobial agents and compromised vasculature that impedes the normal healing process.

One element of the chronic wound infection condition that impedes healing is the formation of biofilm. Biofilm is the result of planktonic bacteria forming together and secreting exopolysaccharide (EPS) to adhere and protect the colonizing community. At the height of formation, EPS can make up between 75-90% of the total biofilm composition (Regt). Biofilm inhibits healing by creating an optimal condition for bacteria to grow, while simultaneously preventing antimicrobial agents from direct access to bacteria.

Methods to remove biofilm include ultrasonic debridement, topical antimicrobials, suction, and surface cleansing. Each of these methods alone treat an aspect of biofilm. For example, ultrasonic debridement of wounds has proven to be the most effective mechanism in disrupting and debulking a majority of the biofilm formation. Yet even in this preferred method, biofilm debris can be left behind to propagate. Suction alone has not proven to be effective in removing biofilm, and can potentially interfere with the operation of other methods like ultrasonic debridement if applied simultaneously.

U.S. Pat. No. 7,608,054 to Soring et al. describes a medical treatment apparatus that combines an ultrasound sonotrode with a suction sheath. The fixed position between the tip of the suction and the tip of the sonotrode only allows for one simultaneous operation. In particular this approach is limited due to the potential interference of the suction tip during the ultrasonic debridement operation.

U.S. Pat. No. 7,522,955 B2 to Rontal et al. describes a method and apparatus for ultrasonic cleaning of biofilm coated surfaces for sinus cavities within a human head. The method describes an ultrasonic application in combination with irrigation and suction that is designed to not remove any of the surrounding underlying tissue. This differs significantly from an ultrasonic debridement of a wound bed, which requires the removal of tissue in combination with biofilm. Thus the ultrasonic probe needs to operate in a cavitation mode at the surface of a wound, causing expulsion of the biofilm.

Methods of mechanical removal of biofilm in wounds alone have proven to be inadequate. What does not exist and what would be beneficial to the market is a method to remove biofilm and prevent it from reforming in order to allow wounds to heal.

OBJECTS OF THE INVENTION

It is an object of the present invention to provide a method to inhibit biofilm formation in order to allow wounds to heal more expeditiously.

A related object of the present invention is to provide a method for removing biofilm so as to reduce the likelihood of the biofilm reforming.

Another related object of the present invention is to provide a method to remove biofilm and prevent it from reforming in order to allow wounds to heal.

An associated object of the present invention is to provide apparatus for removing biofilm with structure to assist in biofilm reformation reduction.

Another associated object of the present invention is to provide apparatus for inhibiting the formation of biofilm.

Although every feature of the invention is attained in at least one embodiment of the invention, there is not necessarily any one embodiment that achieves all of the objects of the invention.

SUMMARY OF THE INVENTION

The present invention broadly contemplates a method for the inhibition of biofilm, a method for reducing the likelihood of biofilm formation. The method includes a surgical room cleansing process and a disruption and removal. The method typically includes a mechanical debridement for the removal of any existing necrotic tissue, surface infection or previously formed biofilm. The mechanical debridement process results in a clean wound bed of healthy granulated tissue. Substantially immediately following the mechanical debridement of a wound, an ultrasound biofilm disrupter pad is placed on or near the wound to prevent bacterial adherence to the wound bed by excretion of EPS.

The ultrasound biofilm disrupter prevents adherence of bacteria to the wound by application of surface acoustic waves at a sufficient frequency and amplitude to disrupt formation but below a threshold that stimulates bacterial growth. In order to accomplish this, a wound-dressing device, which incorporates a disposable ultrasonic transducer, is applied to the wound site post debridement for duration sufficient to allow healing to occur.

In a preferred embodiment ultrasound is used in the debridement process to mechanically remove necrotic tissue while cleansing the wound bed. The ultrasonic debridement should be in the 20 kHz frequency range in order to simultaneously begin the process of biofilm disruption. Once the mechanical debridement is complete, a lower energy setting on the debridement probe may be utilized to pre-condition the wound bed for disrupting adherence or starting the formation of biofilm. Preferably, the wound bed is immediately covered with a wound dressing that incorporates an ultrasonic biofilm disrupter transducer delivering a surface acoustic wave at 20 kHz with an acoustic power output of 0.2-0.4 w/cm$^2$. The transducer is connected to a portable energy source. The energy source can be battery supplied. The wound dressing can incorporate an antimicrobial agent that is delivered during the biofilm disruption treatment.

In another embodiment ultrasound is incorporated into the wound dressing and applied after standard wound cleansing protocols have been administered. These protocols can include saline wash, topical antimicrobial agents applied. The combination of ultrasonic debridement, low-pulsed ultrasonic biofilm disruption and topical antimicrobials produces an important sequential approach to the management and removal of biofilm. The removal of biofilm results in the removal of an impediment to the wound healing process.

In another embodiment ultrasound is combined with suction to create an optimal combination for disruption and removal of biofilm. One stage of biofilm is an excretion of seeding stage. So existing debridement processes can result in a bulking of the biofilm, but at the same time a seeding of the newly created wound bed. The seeding process can occur from a mechanical debridement alone. In this the process for biofilm disruption is temporary at best. To correct this problem, ultrasonic debridement is combined with a suction process that collects the mechanically removed biofilm remnants or seeding agents.

In one embodiment of this combined ultrasound and suction approach, the ultrasonic debridement probe is housed by a suction probe that operates in two stages. The first stage is with the ultrasonic debridement probe engaged with the tissue and the suction tip surrounding the debridement tip so that it is in near contact to the tissue simultaneously to remove the mechanically disrupted biofilm. In the second stage of operation the suction tip can be moved to a position that is not in contact or near contact with the tissue, but sufficient enough to capture any biofilm debris that is propelled into the area.

In another embodiment the combination of ultrasound and suction may have one or more stages of operation. The positioning of the suction tip in relationship to the ultrasound tip can be configured for a variety of different combinations to cause better mechanical disruption and capture of that disrupted biofilm. The combination of both ultrasonic energy to cause debridement and suction to cause removal can be done in a variety of different sequences. For example, ultrasonic mechanical debridement can be performed on the majority of the wound bed prior to engaging suction to capture any remnant amounts of biofilm on the wound bed. In another embodiment the ultrasonic mechanical debridement is performed simultaneous to applying suction either at the tip or near the tip.

In another embodiment the suction is incorporated into the ultrasonic debridement probe to allow for a mechanical disruption and capture of the biofilm. In one embodiment the suction is at the periphery of the ultrasonic debridement probe to allow for maximum capture of the mechanically disrupted biofilm.

In another embodiment, the suction is interspersed throughout the ultrasonic debridement probe so that any area of mechanical disruption has a corresponding area of capture capability.

In another embodiment, a disposable sheath incorporates a suction capability for capturing biofilm during an ultrasonic debridement. In one embodiment the sheath has a multiple position for use during an ultrasonic debridement. The sheath can capture both the debris that is expelled during the debridement and any remaining debris at the surface of the wound bed The sheath can then be disposed of to avoid risk of cross contamination. The sheath may incorporate a sealing strategy to maintain suction pressure while still allowing for multi positioning on the suction tip in relationship to the ultrasonic debridement tip.

Accordingly, a medical therapeutic method pursuant to one aspect of the present invention utilizes an ultrasonic debridement instrument having an operative tip and a suction channel. The method comprises (i) manipulating the instrument to place the operative tip against a patient's tissues at a preselected surgical site, (ii) during contact of the operative tip with the patient's tissues, generating an ultrasonic standing wave in the instrument, thereby fragmenting necrotic tissue and undesired organic material at the surgical site, (iii) during the generating of the ultrasonic standing wave, disposing a suction inlet at a distal end of the suction channel proximate the surgical site and (iv) applying vacuum or negative pressure to the suction channel to remove tissue debris fragmented organic material from the surgical site via the suction inlet, (v) disposing a suction port at a position spaced from the surgical site, and (vi) during and/or after the generating of the ultrasonic standing wave and the fragmenting of tissue and material, sucking ambient air from a region about the surgical site through the suction port at the position.

Preferably, the suction port is provided on the ultrasonic debridement instrument, and the method includes operating an actuator to enable the sucking of air through the suction port.

In one embodiment of the instrument, the actuator may include a sheath or sleeve which is slidably mounted to the instrument for longitudinal motion alternately in opposing directions along the shaft or probe portion thereof. The operating of the actuator then includes shifting the sheath or sleeve in a proximal direction along the instrument. Where the instrument includes a longitudinally shiftable sheath or sleeve, with the suction channel being located between the sheath or sleeve and a shaft or horn of the instrument, the suction inlet and the suction port may both be defined by the distal end of the sheath or sleeve, the position of the sleeve determining whether an intake opening is located at the operative tip of the instrument, and is thus the suction inlet, or is spaced from the operative tip and is therefore the suction port. Accordingly, the method may further comprise shifting the sheath or sleeve in a proximal direction after the applying of a vacuum or negative pressure and prior to the sucking of the ambient air through the suction port, a distal tip of the sheath or sleeve defining the suction inlet in a distal position of the sheath or sleeve, the distal tip defining the suction port in a proximal position of the sheath or sleeve.

In one or more alternative embodiments the suction inlet and the suction port may be different and always mutually spaced from one another. If the instrument includes a slidable sheath or sleeve, the position of that element may determine whether the suction inlet and/or the suction port is active. Thus, the sheath or sleeve may include valves for opening and closing air pathways extending to the suction inlet and the suction port, in dependence on the longitudinal position of the sheath or sleeve. Alternatively, valves may be operated separately via respective electromechanical actuators so that the opening and closing of the suction inlet is controllable independently of the opening and closing of the suction port.

Thus, where the suction port is different from the suction inlet, the suction port being located proximally along the instrument from the suction input, the operating of the actuator may include directing suction under-pressure to the suction port. The actuation may include operating a valve to open a suction pathway to the suction port.

In accordance with another feature of the invention, the method may alternatively or additionally comprise placing an ultrasonic transducer on the patient at least proximate the surgical site after terminating of a debridement process and while the surgical site is free of discernible bacteria. Typically, the transducer is placed immediately after the surgical site has been cleaned of necrotic tissue and other undesirable debris and even prior to the removal of the patient from the operating room. After the placing of the transducer and while the transducer is in effective vibration-transmitting contact with the patient, an electrical energization waveform of an ultrasonic frequency is conducted to the transducer at least intermittently during a period of approximately one day or longer to prevent biofilm formation on the patient at the surgical site and facilitate a healing of the patient's tissue at the surgical site.

The transducer may be affixed to a carrier pad, the placing of the transducer on the patient including attaching the pad to the patient. Alternatively, the transducer may be disposed in a balloon or bladder inflated with a gel or other medium conducive to the effective transmission of ultrasonic pressure waves, the balloon or bladder being attached to the patient over or adjacent the surgical site. Other transducer carriers and methods of attachment to the patient will occur to those skilled in the art.

Accordingly, a medical therapeutic method comprises (a) removing necrotic tissue and undesired organic material from a surgical site on a patient, (b) shortly thereafter, while the surgical site is free of discernible bacteria, placing at least one ultrasonic transducer on the patient at least proximate the surgical site, and (c) after the placing of the transducer and while the transducer is in effective vibration-transmitting contact with the patient, conducting an electrical energization waveform of an ultrasonic frequency to the transducer at least intermittently during a period of approximately one day or longer, the waveform having frequency, amplitude and duration to effectively reduce formation on the patient at the surgical site and thereby facilitate a healing of the patient's tissue at the surgical site. The placing of the transducer preferably includes removably attaching the transducer to the patient atop tissues at the surgical site.

A surgical device comprises an ultrasonic probe having an operative tip, an electromechanical transducer operatively connected to the probe for generating an ultrasonic standing wave in the probe, and at least one sheath or sleeve disposed about the probe and defining at least a first suction port at a distal end of the probe, proximate the operative tip, and a second suction port spaced from the distal end of the probe.

The one or more sheaths or sleeves may take the form of exactly one sheath or sleeve slidably attached to the probe to shift between a distal position and a proximal position, wherein a distal end of the sheath or sleeve is alternately locatable (i) proximate the operative tip to define the first suction port and (ii) at a predetermined distance from the operative tip to define the second suction port.

Alternatively, the first suction port and the second suction port are different openings in the at least one sheath or sleeve. Their operational status may be separately controlled via respective valves. Moreover, the suction ports may be connectable to vacuum sources of different strengths. The magnitude of the vacuum or negative pressure applied to the proximal port is typically greater than the magnitude of the vacuum or negative pressure applied to the distal port.

The sheath or sleeve may define a first suction channel extending to the first suction port and a separate second suction channel extending to the second suction port, the first suction channel and the second suction channel being subjectable to different negative pressures.

DETAILED DESCRIPTION

Figure 1:
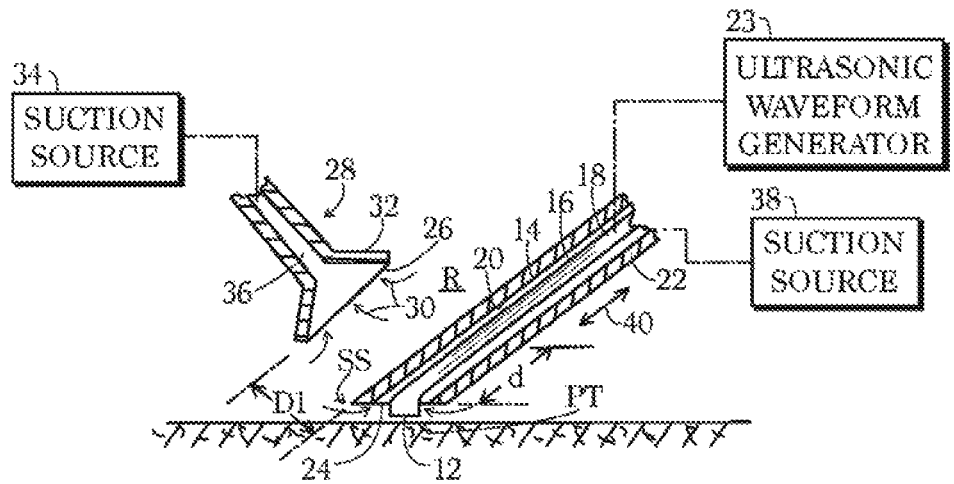
FIG. 1 is partially a schematic cross-sectional view and partially a block diagram of a system for removing biofilm from a wound site and reducing the likelihood of biofilm reformation thereafter.

The present disclosure contemplates a two phase method for reducing the formation of biofilm. The first phase is performed where a wound site is being treated for removal of necrotic tissue, eschar or biofilm and includes an evacuation of ambient air from a region about the surgical or treatment site, to extract airborne or aerosolized bacteria ejected from the site by the treatment. The extracted bacteria are prevented from settling back onto the cleansed tissue surface, thus at least reducing colonial bacteriological growth and concomitantly exuded biofilm material. The second phase or approach for reducing biofilm involves the attachment of one or more ultrasonic transducers to the patient over or near a surgical treatment site after the surgery is terminated. Each applied ultrasonic transducer is used to vibrate the patient's tissues at the treatment site to disrupt biofilm formation. The two phases of treatment may be used separately depending on the application. Thus, ultrasonic biofilm disruption may be used at wound sites which have not been subjected to formal processes for removal of necrotic tissue, eschar or biofilm.

Accordingly, a medical therapeutic method may utilize an ultrasonic debridement instrument 10 (FIG. 1) having an operative tip or surface 12 and a suction channel 14 defined between an outer surface 16 of an ultrasonic horn 18 and an inner surface 20 of a cannula or sheath 22. The method comprises manipulating the instrument 10 to place the operative tip or surface 12 against a patient's tissues PT at a preselected surgical site SS. During contact of the operative tip 12 with the patient's tissues PT, one operates a waveform generator 23 to generate an ultrasonic standing wave in the instrument 10 and particularly in probe or horn 18, to thereby fragment necrotic tissue and undesired organic material at the surgical site SS. During the generating of the ultrasonic standing wave, a suction inlet 24 at a distal end of the suction channel 14 is disposed proximate the surgical site SS and a vacuum or negative pressure is applied to the suction channel 14 to suck tissue debris and fragmented organic material from the surgical site SS via the suction inlet 24. A suction port 26 of another instrument 28 is disposed at a position spaced at a distance D1 from the surgical site SS. During and/or after the generating of the ultrasonic standing wave and the fragmenting of tissue and material by instrument 10, instrument 28 is operated to suck ambient air, as indicated by arrows 30, from a region R about the surgical site SS through suction port 26. While suction inlet 24 is typically located between 1 and 5 mm from the surgical site SS and the tissue surface at the surgical site, suction port 26 is typically located 2-6 cm from the tissue surface at the surgical site SS.

As depicted in FIG. 1, instrument 28 may be formed at a distal end with an enlarged or expanded extension 32, such as a cone, to funnel air 30 into the instrument. A suction source or vacuum generator 34 communicating with a lumen 36 of instrument 28 may exert a greater suction force than that of a suction source or vacuum generator 38 communicating with suction channel 14.

In an alternative approach, instrument 28 is omitted. Instead, cannula or sheath 22 is shiftably mounted to probe or horn 18 for longitudinal motion alternately in opposing directions along the shaft or probe portion thereof, thereby enabling the user to position the suction port, defined in part by the distal edge of the sheath, in two or more alternative locations, a most distal location adjacent the operative tip 18 of the probe or horn 12 and a more proximal location. As indicated by a double headed arrow 40, cannula or sheath 22 is pulled in a proximal direction after an operation removing tissue or other organic matter from surgical site SS so that suction port 26 is located at a distanced from the operative tip or surface 12 of instrument 10. An actuator such as suction source 38, or a switch component thereof, is operated to enable the sucking of air through suction port 26 at the retracted position of cannula or sheath 22. In a simple configuration, suction source 38 may have two operating states, on and off, the position of sheath 22 determining whether suction is applied at the surgical site SS or at a distance therefrom. In a slightly more complicated configuration, suction source 38 may be provided with three operating states, namely, off, high suction and low suction. The degree of suction may be selectable by the operator or may be automatically controlled in accordance with the longitudinal or axial position of sheath 22 along probe or horn 12. For instance, sheath or sleeve 22 may be provided with valves (not shown) for opening and closing air pathways in dependence on the longitudinal position.

Figure 2:
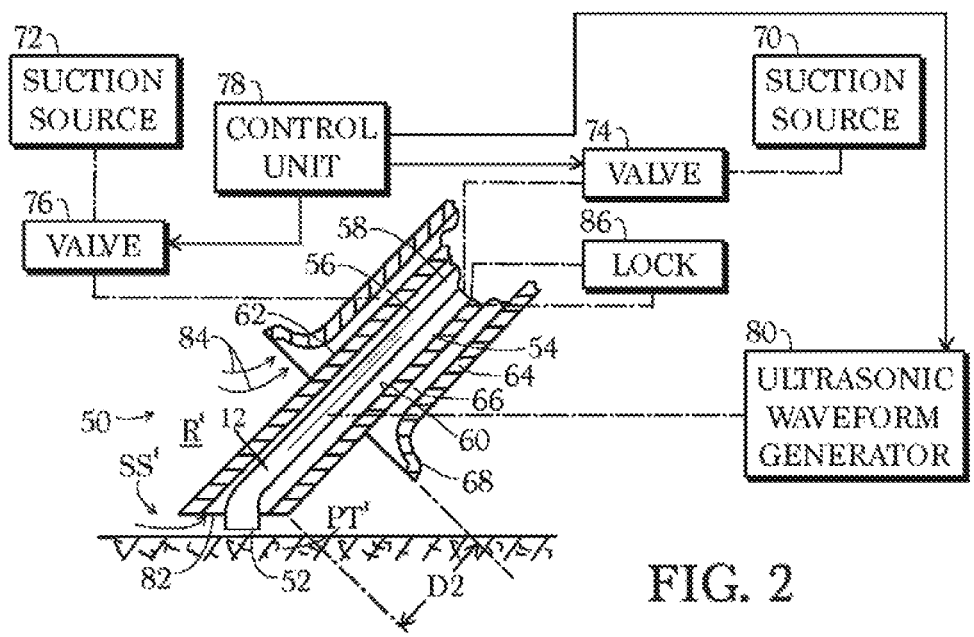
FIG. 2 is partially a schematic cross-sectional view and partially a block diagram of another apparatus for removing biofilm from a wound site and reducing the likelihood of biofilm reformation thereafter.

An alternative instrument assembly 50 depicted in FIG. 2 has an operative tip or surface 52 and a suction channel 54 located between an outer surface 56 of an ultrasonic horn 58 and an inner surface 60 of a first or inner sheath 62. A second, outer, sheath 64 surrounds the first sheath 62 and defines therewith a second suction channel 66 for the evacuation of ambient air from a sizable region R' about the surgical site SS, exemplarily through a conical port element 68 at the distal end of the outer sheath 64. The two suction channels 54 and 66 may be connected to respective suction sources or vacuum generators 70 and 72 via respective valves 74 and 76 both actuatable by the operator via a control unit 78. Control unit 78 is tied to a control input (not separately designated) of an ultrasonic waveform generator 80 that is operatively connected to probe or horn 12 via an electromechanical transducer (not shown) such as a stack of piezoelectric crystals. Control unit 78 may be programmed to open valve 76 within a selectable time interval after the opening of valve 74 and the activation of waveform generator 80.

In a surgical procedure, instrument assembly 50 is manipulated to place the operative tip or surface 52 against patient's tissues PT' at a preselected surgical site SS'. During contact of the operative tip 52 with the patient's tissues PT', control unit 78 is operated to activate waveform generator 80, which generates an ultrasonic standing wave in probe or horn 58, to thereby fragment necrotic tissue and undesired organic material at the surgical site SS'. During the generating of the ultrasonic standing wave, a suction inlet 82 at a distal end of inner suction channel 54 is disposed proximate the surgical site SS' and a vacuum or negative pressure is applied by suction source 70 to the suction channel 54 via valve 74 to suck tissue debris and fragmented organic material from the surgical site SS' through the suction inlet 82. Conical port element 68 is disposed at a distance D2 from the surgical site SS'. During and/or after the generating of the ultrasonic standing wave and the fragmenting of tissue and material by instrument 50, vacuum generator 72 and valve 76 are actuated by control unit 78 to suck ambient air, as indicated by arrows 84, from region R' through suction port or cone 68. Suction inlet 82 is typically located a minimal distance, exemplarily between about 1 and about 5 mm, from tissues at the surgical site SS' while suction port 68 distance D2 is typically 2-6 cm from the surgical site SS'.

Outer sheath 64 may be temporarily fixed to inner sheath 62 via a quick-release lock 86 such as a set screw. Thus, the relative axial positions of sheaths 62 and 64 may be adjusted to change distance D2. Control unit 78 may be connected to suction sources or vacuum generators 70 and 72 for varying the power usage thereof and average magnitudes of the negative pressures generated thereby.

Figure 3:
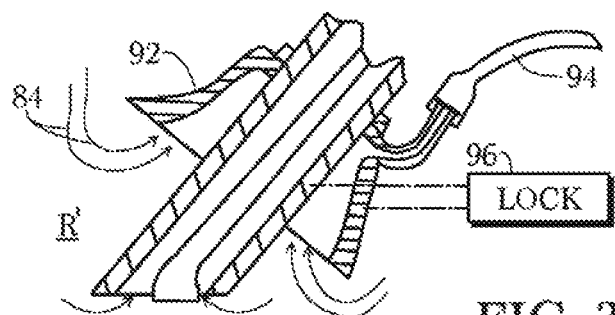
FIG. 3 is partially a schematic cross-sectional view and partially a block diagram of yet a further apparatus for removing biofilm from a wound site and reducing the likelihood of biofilm reformation thereafter.

FIG. 3 illustrates a modification 90 of the instrument assembly 50 of FIG. 2. Instead of outer sheath 64, a suction nozzle 92 is attached to sheath 62. Nozzle 92 is connected to suction source or vacuum generator 72 via a reinforced hose 94. Nozzle 92 is removably secured to sheath 62 via a locking element 96 such as a ring clamp or a set screw. The operation of modified instrument 90 is as discussed above.

The present method alternatively or additionally comprises placing an ultrasonic transducer 102 (see, e.g., FIGS. 4 and 5) in effective contact with a patient TP at least proximate a surgical site SI after terminating of a debridement or other tissue cleaning procedure and while the surgical site SI is free of discernible bacteria. Typically, transducer 102 is placed immediately after the surgical site SI has been cleaned of necrotic tissue and other undesirable debris and even prior to the removal of the patient TP from the operating room. After the placing of transducer 102 and while the transducer is in effective vibration-transmitting contact with the patient TP, an electrical energization waveform of an ultrasonic frequency is conducted from a waveform generator 104 to transducer 102 at least intermittently during a period of approximately one day or longer to reduce, if not prevent, biofilm formation on the patient at the surgical site SI and thereby facilitate a healing of the patient's tissue at the surgical site.

Figure 4:
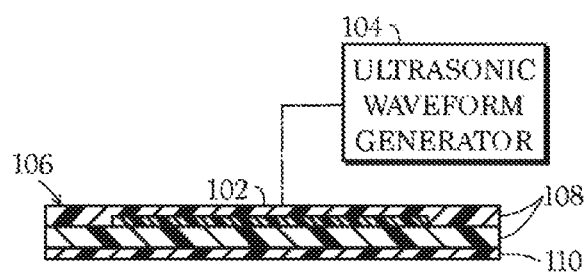
FIG. 4 is partially a schematic cross-sectional view and partially a block diagram of a device for attachment to a patient at a wound site, to reduce the likelihood of biofilm formation on the wound site.
Figure 5:
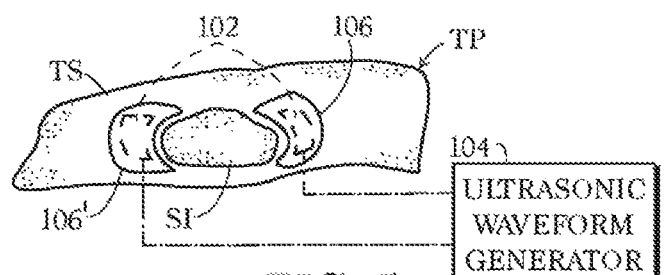
FIG. 5 is a schematic top plan view and partially a block diagram of the device of FIG. 4, in position and attached to a patient at a wound site on the patient.
Figure 6:
FIG. 6 is a schematic perspective view of another device for attachment to a patient at a wound site, to reduce the likelihood of biofilm formation.

As depicted in FIG. 4, transducer 102 may be affixed to a carrier pad 106, exemplarily sandwiched between layers 108 of a biocompatible and ultrasound transmitting material. The placing of transducer 102 on the patient TP preferably includes attaching pad 106 to the patient, for example, via an adhesive layer 110. As depicted in FIG. 5, pad 106 is disposed alone or together with one or more other carrier pads 106', on a tissue surface TS proximate surgical site SI. Alternatively, pad 106 may be placed directly over the surgical site SI shortly, if not immediately, after tissue removal is complete. In that case adhesive layer 110 may be omitted in favor of a layer of gel. The gel may be oxygenated and contain antibiotics. As depicted in FIG. 6, straps or bands 112 may be provided for securing the pad 106 to the patient TP.

Figure 7:
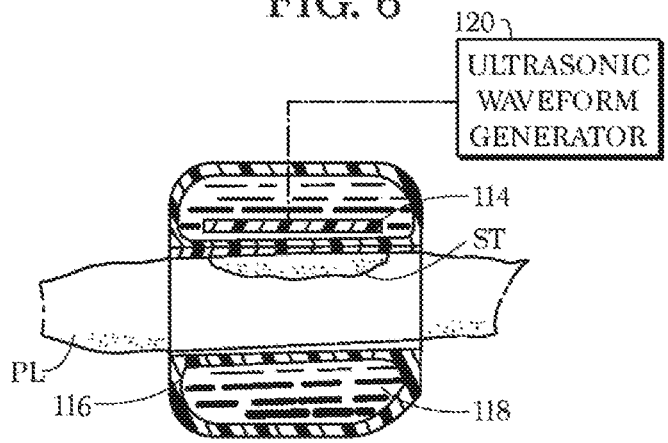
FIG. 7 is partially a schematic cross-sectional view and partially a block diagram of a device for attachment to a patient at a wound site, to reduce the likelihood of biofilm formation on the wound site, showing attachment of the device to a patient's limb.

Alternatively, as depicted in FIG. 7, an electromechanical, specifically, a piezoelectric, transducer 114 may be disposed inside a balloon or bladder 116 inflated with a gel or other medium 118 conducive to the effective transmission of ultrasonic pressure waves, the balloon or bladder being attached to a patient TP' over or adjacent a surgical site SI'. Balloon or bladder 116 is affixed to a patient, e.g., around an arm or leg PL, over or near a surgical site ST and an ultrasonic waveform generator 120 is activated to generate ultrasonic vibrations conducted into the patient's tissue to disrupt biofilm formation. Other transducer carriers and methods of attachment to the patient will occur to those skilled in the art.

A medical therapeutic method utilizing one or more of the transducer devices shown in FIGS. 4-7, first comprises cleaning surgical site SI or ST of necrotic tissue and undesired organic material, for instance via ultrasonic debridement and suction as discussed above with reference to FIGS. 1-3. Shortly thereafter, while the surgical site SI or ST is free of discernible bacteria, one places at least one ultrasonic transducer 102, 114 on the patient TP, TP' proximate or on the surgical site SI, ST, and thereafter, while the transducer is in effective vibration-transmitting contact with the patient TP, TP', conducting an electrical energization waveform of an ultrasonic frequency to the transducer 102, 114 at least intermittently during a period of approximately one day or longer. The waveform has frequency, amplitude and duration parameters selected to effectively reduce biofilm formation on the patient TP, TP' at the surgical site SI, ST and thereby facilitate a healing of the patient's tissue at the surgical site. The ultrasound generates a surface acoustic wave at 20 kHz with an acoustic power output of 0.2-0.4 w/cm$^2$. The treatment period is long enough to enable healthy tissue formation. The placing of the transducer 102, 114 preferably includes removably attaching the transducer to the patient atop tissues at the surgical site SI, ST.

What is claimed is:

1. A medical therapeutic method comprising:
removing necrotic tissue and undesired organic material from a surgical site on a patient;
after the removal of all discernible necrotic tissue and undesirable organic material from the surgical site and while the surgical site is free of discernible bacteria, placing at least one ultrasonic transducer on the patient at least proximate the surgical site; and
after the placing of said transducer and while said transducer is in effective vibration-transmitting contact with the patient, conducting an electrical energization waveform of an ultrasonic frequency to said transducer at least intermittently during a period of approximately one day or longer, said waveform having frequency, amplitude and duration to effectively reduce biofilm formation on the patient at the surgical site and thereby facilitate a healing of the patient's tissue at the surgical site.

2. The method defined in claim 1 wherein the placing of said transducer includes removably attaching said transducer to the patient.

3. The method defined in claim 2 wherein the placing of said transducer includes removably attaching said transducer atop tissues at the surgical site.

4. The method defined in claim 2 wherein said transducer is affixed to a carrier pad, the placing of said transducer on the patient including attaching said pad to the patient.

5. The method defined in claim 1 wherein the removing of necrotic tissues includes operating an ultrasonic debrider instrument at a first energy setting, further comprising utilizing said instrument at a lower second energy setting to pre-condition the tissues at the surgical site for disrupting adherence or starting the formation of biofilm.

* * * * *